(12) United States Patent
Pallone

(10) Patent No.: US 11,219,545 B2
(45) Date of Patent: *Jan. 11, 2022

(54) SPINE SUPPORT DEVICE FOR MAINTAINING ANATOMICAL ALIGNMENT AND STABILITY

(71) Applicant: Kevin Pallone, Parkland, FL (US)

(72) Inventor: Kevin Pallone, Parkland, FL (US)

( * ) Notice: Subject to any disclaimer, the term of this patent is extended or adjusted under 35 U.S.C. 154(b) by 469 days.

This patent is subject to a terminal disclaimer.

(21) Appl. No.: 16/427,509

(22) Filed: May 31, 2019

(65) Prior Publication Data

US 2019/0282389 A1  Sep. 19, 2019

Related U.S. Application Data

(63) Continuation-in-part of application No. 15/133,361, filed on Apr. 20, 2016, now Pat. No. 10,342,692.

(51) Int. Cl.

| A61F 5/02 | (2006.01) |
|---|---|
| A61F 7/00 | (2006.01) |
| A61F 7/08 | (2006.01) |
| A61F 7/10 | (2006.01) |
| A61F 5/058 | (2006.01) |
| A61F 7/02 | (2006.01) |
| A61B 5/00 | (2006.01) |
| A61B 5/107 | (2006.01) |

(52) U.S. Cl.
CPC ............ *A61F 5/026* (2013.01); *A61B 5/4566* (2013.01); *A61F 5/028* (2013.01); *A61F 7/02* (2013.01); *A61B 5/107* (2013.01); *A61B 2562/0261* (2013.01); *A61F 5/024* (2013.01)

(58) Field of Classification Search
CPC ........ A61F 5/028; A61F 7/10; A61F 5/05883; A61F 5/024; A61F 7/08; A61F 2007/0024
USPC .......................................................... 602/19
See application file for complete search history.

(56) References Cited

U.S. PATENT DOCUMENTS 10,342,692 B2 * 7/2019 Pallone ............... A61F 5/05883

* cited by examiner

*Primary Examiner* — Tarla R Patel

(74) *Attorney, Agent, or Firm* — Glenn E. Gold, P.A.; Glenn E. Gold

(57) ABSTRACT

A spine support device includes a support plate having front and rear faces, a central opening, and a pair of stabilizing stirrups formed on the rear face of the support plate in spaced parallel relationship to augment the support provided by the support plate when positioned at its front face in contact with a portion of a person's back surrounding a region of spinal vertebra visible through the central opening in the support plate. The support plate has opposing inner side edge portions at opposing sides of the central opening and opposite peripheral side edge portions spaced outwardly therefrom with the stabilizing stirrups therebetween. The opposing inner side edge portions and the opposite peripheral side edge portions of the support plate have respective alternating peak and valley shapes for accommodating interconnecting facets of the spinal vertebra region visible through the central opening in the support plate.

20 Claims, 14 Drawing Sheets

SPINE SUPPORT DEVICE FOR MAINTAINING ANATOMICAL ALIGNMENT AND STABILITY

CROSS REFERENCE TO RELATED APPLICATIONS

This application is a continuation-in-part of co-pending U.S. patent application Ser. No. 15/133,361, having a filing date of Apr. 20, 2016, the entire contents of which are incorporated by reference herein.

FIELD OF THE INVENTION

The present invention relates generally to human spine support devices and, more particularly, is concerned with such spine support devices intended for use by individuals to correct anatomically improper spinal alignment, for maintaining anatomically proper spinal alignment and normal spinal curvature, and for imparting spinal stability for relief of lower back pain and neck pain.

BACKGROUND OF THE INVENTION

Low back pain is one of the most common health issues people face. In the United States alone, approximately 60% to 80% of the adult population suffers from low back pain and/or neck pain. Back pain is the leading cause of disability in Americans under 45 years of age. It is the second most common reason people cite for seeking medical attention. Every year, approximately 13 million people seek medical treatment for chronic back pain. The condition leaves about 2.4 million Americans chronically disabled, and another 2.4 million temporarily disabled. Approximately $90 billion is spent on the diagnosis and management of low back pain, with an additional $10-20 billion of annual economic losses attributed to the corresponding reduction in worker productivity. Lower back and neck pain is caused, in most cases, by poor anatomical spinal alignment. Someone living with poor spinal alignment may suffer from restricted spine flexibility, instability and reduced strength. More often than not, these conditions lead to pain, discomfort and stiffness, which can minimize and negatively affect an individual's quality of life as they go about doing everyday functional activities.

In most cases, low back and neck pain are the direct result of poor anatomical spinal alignment. Individuals living with poor spinal alignment may suffer from restricted spinal flexibility, spinal instability, and reduced strength. These conditions often lead to chronic pain, discomfort and stiffness, which correspondingly reduce, and otherwise negatively impact, the affected individual's quality of life while going about normal, everyday functional activities, recreational activities, work-related activities, sports-related activities, and the like.

Elastic therapeutic tape, commonly referred to as "kinesiology tape," is a widely used approach for addressing muscle and joint pain and disability; particularly, among athletes. A major drawback, or shortcoming, commonly associated with taping is that it is too flimsy and oftentimes does not provide adequate structural support. It is used primarily as a feedback mechanism while attached to the skin in order to prevent the occurrence of an abnormal, or otherwise undesirable, posture. However, taping does not adequately restrict motion, nor prevent an individual from maintaining an abnormal, or undesirable, posture because the tape's inherently high degree of structural flexibility precludes its use for providing sufficient anatomical support and/or maintaining proper anatomical alignment. Other conventional approaches, which are inherently more structurally sound than tape, include the use of braces and adhesive foam supports. However, conventional braces and adhesive supports typically lack an accurate anatomical design, fail to incorporate means for conforming to the unique anatomical variations from person to person, restrict an individual user's optimal range of motion, and provide less-than-optimal support of the spine. Furthermore, donning conventional bracing presents a host of additional issues; for example, bracing is often cumbersome, difficult to apply, and, because it is normally worn over clothing, causes the individual wearer to become uncomfortably hot and sweaty. Likewise, adhesive foam supports are generally uncomfortable and restrict, or limit, proper anatomic range of motion. Furthermore, these and other known approaches are not designed to mimic, or conform to, the normal anatomy of the human spine. Consequently, currently-available products and associated methods do not allow for appropriate degrees of freedom of motion, or movement, of the spine in an anatomically correct manner, do not provide optimal desired spinal support, and do not provide means for correcting male alignment.

Accordingly, there remains a need in the art for an innovation that will overcome the aforementioned deficiencies and limitations of known devices, products and methods.

SUMMARY OF THE INVENTION

The present invention is directed to an innovation that overcomes the deficiencies of the known art and the problems that remain unsolved by providing a spine support device for maintaining and correcting anatomical alignment and stability for preventing back and neck pain and for relieving existing back and neck pain. The spine support device provides a physical/mechanical support to the spine which can be easily applied before, during or after an exercise or non-exercise activity in order to maintain proper alignment of the spine; thereby, improving a person's natural spine support in order to prevent future neck and back pain or to reduce existing neck and back pain. The unique structural design of the spine support device conforms to the natural anatomy of the spine, facilitating proper anatomical posture and enabling rotation of the spine while providing the stability and support the spine needs to function properly.

Generally, the present invention is directed to a spinal support system, including:

a pliable support plate partially defined by a contiguous peripheral edge adjoining front and rear support plate faces, and a vertically-oriented longitudinal opening extending completely therethrough, the opening having a geometric area defined by a contiguous support plate interior edge and particularly sized and shaped to define a central opening area for visibly exposing a desired area of a posterior surface of a user's body overlying a corresponding predetermined spine segment of a device user's spine when the spine support device is affixed to the posterior surface during use, wherein the spine segment includes a contiguous series of individual spinal vertebra and interconnecting facets of said contiguous series of individual spinal vertebra;

an adhesive layer disposed upon the support plate front face for facilitating releasable adhesive attachment of the pliable support plate directly to the posterior surface of the individual; and a pair of vertically-oriented longitudinal stabilizing stirrups integrated with the rear face of said support plate in a spaced-apart parallel relationship to one another, each one of the pair of stabilizing stirrups having a rigidity adequate to impart a predefined desired degree of support augmenting support provided by the support plate following adhesion of the front face of the support plate to said posterior surface of at least one of a back and neck region of the device user's body, the stabilizing stirrups further enabling and facilitating freedom of rotational movement of the corresponding spine segment that remains exposed through the support plate central opening after the spine support device is affixed to the posterior surface of the user.

In an aspect of the invention, the spine support device is provided that is uniquely constructed and configured to facilitate normal curvature of the spine as well as correct abnormal curvature. Furthermore, the spine support device allows for normal rotation of the spine, while concurrently reducing excessive forward bending and rearward extension of a selected length or region thereof.

In another aspect, the spine support device includes a support plate incorporating a series of peripheral edge notches and a corresponding, laterally-aligned, series of interior edge notches that, together, function to accommodate twisting motion of the back and neck about the spinal axis.

In another aspect, the spine support device incorporates a pair of spaced-apart, longitudinally-extending, rigid support rod subassemblies, alternatively referred to as "stabilizing stirrups," which restrict forward bending and rearward extension motion of the back or neck along a length, or segment, of the spine overlaid by the spine support device.

In another aspect, the spine support device incorporates vibration-generating devices for imparting vibrational energy to the back of an individual user.

In another aspect, the spine support device incorporates one or more sensors integrated into at least one of the rigid support rod subassemblies, or stabilizing stirrups, wherein the sensors have sense capabilities and the ability to deform with respective deformation of a corresponding support rod subassembly.

In another aspect, the sensors may include one or more angular displacement sensors, strain sensors, compressive force sensors and haptic sensors, wirelessly communicative with a portable smart device, such as a mobile phone, via an interactive application residing thereon in order to collect and process sensor-related data.

In another aspect, the spine support device may incorporate a medicinal or non-medicinal composition integrated into a layer of chemical adhesive used to attach the device to the user's skin.

In another aspect, a spine support system incorporates a spine support device applicator enabling an individual to accurately apply the spine support device to the lower back or neck region without requiring the assistance of another individual.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION OF EXEMPLARY IMPLEMENTATIONS

Figure 1:
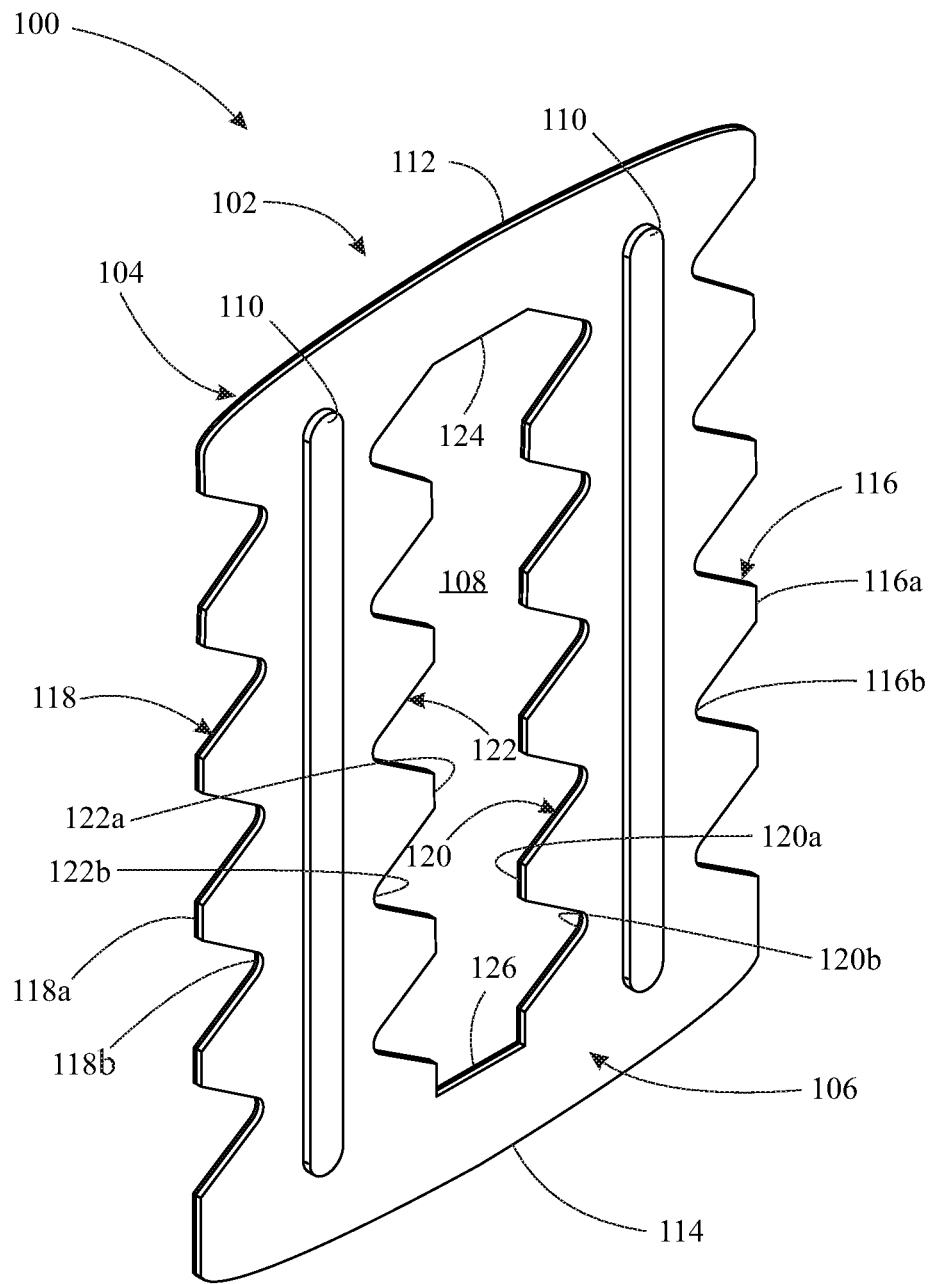
FIG. 1 presents a rear isometric view of a first exemplary implementation of the spine support device of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now to FIGS. 1-4, there is illustrated a first exemplary implementation of a spine support device, generally designated 100, which, in accordance with aspects of the present invention, facilitates maintenance of proper anatomical alignment and stability, and the correction of improper anatomical alignment and stability, for preventing back and neck pain or relieving existing back and neck pain. The spine support device 100 provides physical, mechanical support of a selected region of the spinal vertebra of a person which can be easily applied on the person's back or neck adjacent to the selected region, or length, of the spinal vertebra before, during or after normal activity or an athletic event in order to assist in maintaining and or correcting proper alignment of the spinal vertebra; thereby, improving the person's natural support in order to prevent or reduce back and neck pain. The configuration of the spine support device 100 enables self-adhesive attachment to the person's back and neck. Furthermore, the unique design of the spine support device 100 conforms to the natural anatomy of the spine so as to allow for rotation of the spine and, at the same time, provide the stability and support the spine needs to function properly.

More particularly, the spine support device 100 includes a support plate 102 having a generally flat, or planar, configuration with front and rear faces, 104 and 106, respectively, a central opening 108 extending completely through the front and rear faces of the support plate, and a pair of substantially identical stabilizing stirrups 110, or rods, along a rear face 106 of the support plate 102. The stabilizing stirrups 110 are preferably provided disposed upon, and protruding outwardly from, the rear face 106 of the support plate 102, which has a pliable construction to enable the support plate to temporarily deform to conform to the lower back or neck of an individual while being donned. The stabilizing stirrups 110 are designed having a user-selectable desired stiffness to augment the effectiveness of the support provided by the spine support device 100 when the front face 104 of the support plate 102 is positioned in contact with an area of an individual user's lower back or neck surrounding a selected spinal vertebra region of the individual exposed through the central opening 108 of the support plate 102 intended to be supported by the spine support device 100.

The support plate 102 is further defined by opposite peripheral upper and lower edge portions, 112 and 114, respectively, spaced apart from one another and inwardly spaced a distance from opposite peripheral side edge portions, 116 and 118, adjoining the upper and lower peripheral edge portions. Each of the opposite peripheral side edge portions 116, 118 has an alternating peak-and-valley, or notched, profile, wherein the opposite peripheral side edge profiles are mirror images of one another. In other words, the opposite edge portions 116, 118 incorporate respective opposite peaks 116a, 118a and respective opposite valleys 116b, 118b along their corresponding lengths. Furthermore, support plate 102 incorporates opposing, or inwardly-facing, interior side edges, 120 and 122, respectively, adjoined by respective upper and lower interior edges, 124 and 126, together defining central opening 108. Like the peripheral, or exterior, side edges each of the opposing interior side edges 120, 122 has an alternating peak-and-valley shape, or notched edge profile, such that the opposing inner side edges are also mirror images of one another. In other words, the opposite interior edge portions 120, 122 incorporate respective opposite peaks 120a, 122a and respective opposite valleys 120b, 122b along their corresponding lengths. The peaks 116a, 118a, 120a, 122a and the valleys 116b, 118b, 120b, 122b are all vertically aligned along their respective lengths. This is a very significant feature of the present invention. In particular, this structural feature, or characteristic, defines a series of notches particularly sized and shaped to accommodate corresponding interconnecting facets of a selected spinal vertebra region, or length, desired to be supported by the support plate 102, while enabling twisting of the back and neck about the supported spinal vertebra region.

Preferably, the opposite peripheral upper and lower edges 112, 114 have opposite convex profiles that are mirror images of one another. The convex curved profiles facilitate an anatomical fit below the thoracic spinal region and at the base of the pelvis, when the spine support device 100 is being donned. In particular, the alternating peak-and-valley vertical edge profiles define a plurality of notches (e.g. five notches) specifically matching, or corresponding to, the human lumbar and cervical spinal regions to enable and facilitate rotation of the user's spine while donning the spine support device 100.

Figure 4:
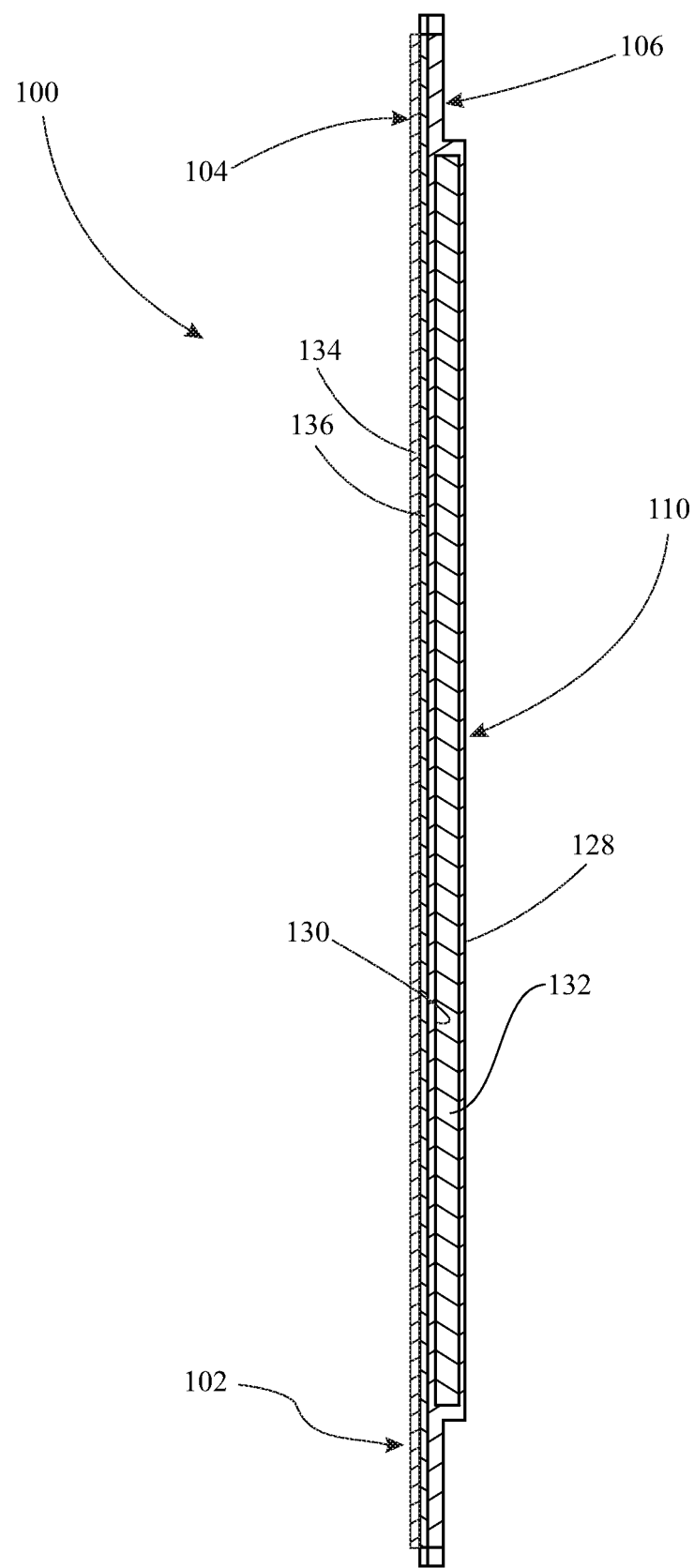
FIG. 4 presents an enlarged longitudinal cross-sectional view of the spine support device 100 taken along section line 4-4 of FIG. 3.
Figure 5:
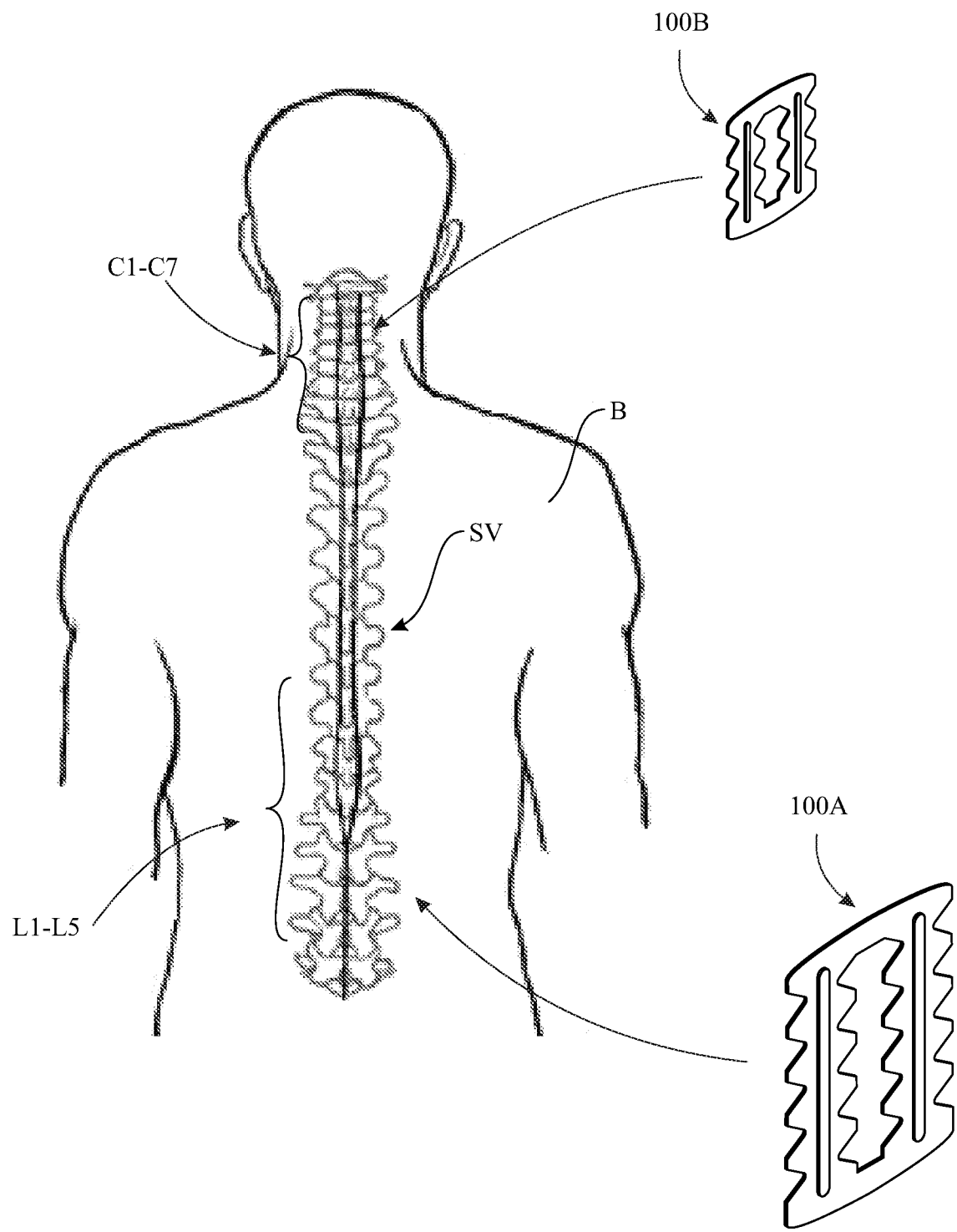
FIG. 5 presents a rear pictorial view of a human spine overlaying the back and neck of an individual body, with arrows and corresponding reference characters identifying particular cervical and lumbar regions of the spine, prior to application of corresponding appropriately-sized spine support devices, such as the exemplary device 100 introduced in FIG. 3.
Figure 6:
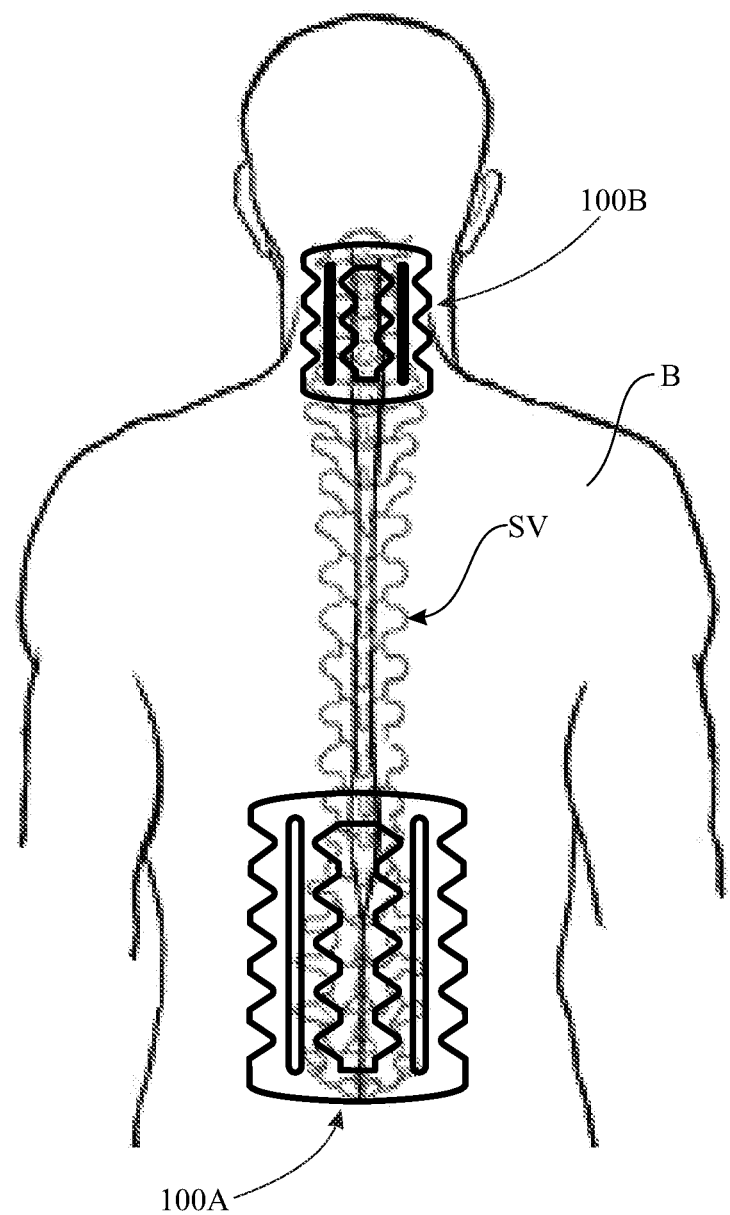
FIG. 6 presents a rear pictorial view of the human spine originally introduced in FIG. 5, showing a pair of appropriately-sized spine support devices 100A and 100B affixed to the corresponding neck and lower back of the aforementioned individual's body, showing the proper positioning and alignment of the device(s) over the respective cervical and lumbar regions.

The pair of stabilizing stirrups 110 protruding from the rear face 106 of the support plate 102 are in spaced-apart parallel relationship to one another, and each is inwardly spaced a desired distance from respective ones of the opposite peripheral side edges 116, 118, and a desired distance from respective ones of the opposing inner side edges 120, 122 of the support plate so as to augment the support provided by the support plate when the latter is positioned in contact with the portion of the person's back (see FIGS. 5 and 6). As best seen in FIG. 4, each of the stabilizing stirrups 110 may include an elongated outer body 128, or housing portion, defining an elongated cavity 130 sized, shaped, and otherwise configured for receiving an elongated inner body 132 therein. Preferably, each elongated outer body 128 defines a corresponding elongated cavity 130 volume substantially conforming to a corresponding geometry of elongated inner body 132. The stabilizing stirrups 110 may be provided in any of a variety of strengths (i.e. having a desired stiffness) in order to provide more or less support depending upon the particular application. The relative rigidity of the stabilizing stirrups 110 may be varied by selecting an inner body 132 having a particular desired stiffness. Stiffness (or rigidity) is a property of polymers that is described by flexural modulus, or bending modulus, of elasticity. Flexural modulus denotes the ability of material to bend. It is a measure of a material's stiffness/resistance to bend when a force is applied perpendicular to the long edge of a sample—commonly referred to as the three-point bend test. Accordingly, where the inner body is manufactured in the form of a plastic molded body the stiffness may be varied by selecting a polymer having the desired flexural modulus. Furthermore, the flexural modulus of a particular material may be varied via the addition of fillers, such as polyolefins, to the polymer system. Alternatively, stiffness may varied by altering the physical structure of the inner body 132. For example, stiffness may be varied by altering the relative thickness of the inner body 132 and/or the geometry of the inner body.

As is well known, the regions of the spine consist of the cervical, thoracic, lumbar, and sacral. The neck region is the Cervical Spine, which consists of seven (7) vertebrae which are abbreviated C1-C7 (top to bottom). These vertebrae protect the brain stem and the spinal cord, support the skull, and allow for a wide range of head movement. Beneath the last cervical vertebra are twelve (12) Thoracic vertebrae abbreviated T1-T12 (top to bottom). The Lumbar Spine consists of five vertebrae abbreviated L1-L5 (top to bottom). The lumbar vertebrae are the largest and carry the most of the body's weight. This region allows more range of motion than the thoracic spine, but less than the cervical. Lumbar facet joints enable significant flexion and extension movement, but limits rotation.

Figure 2:
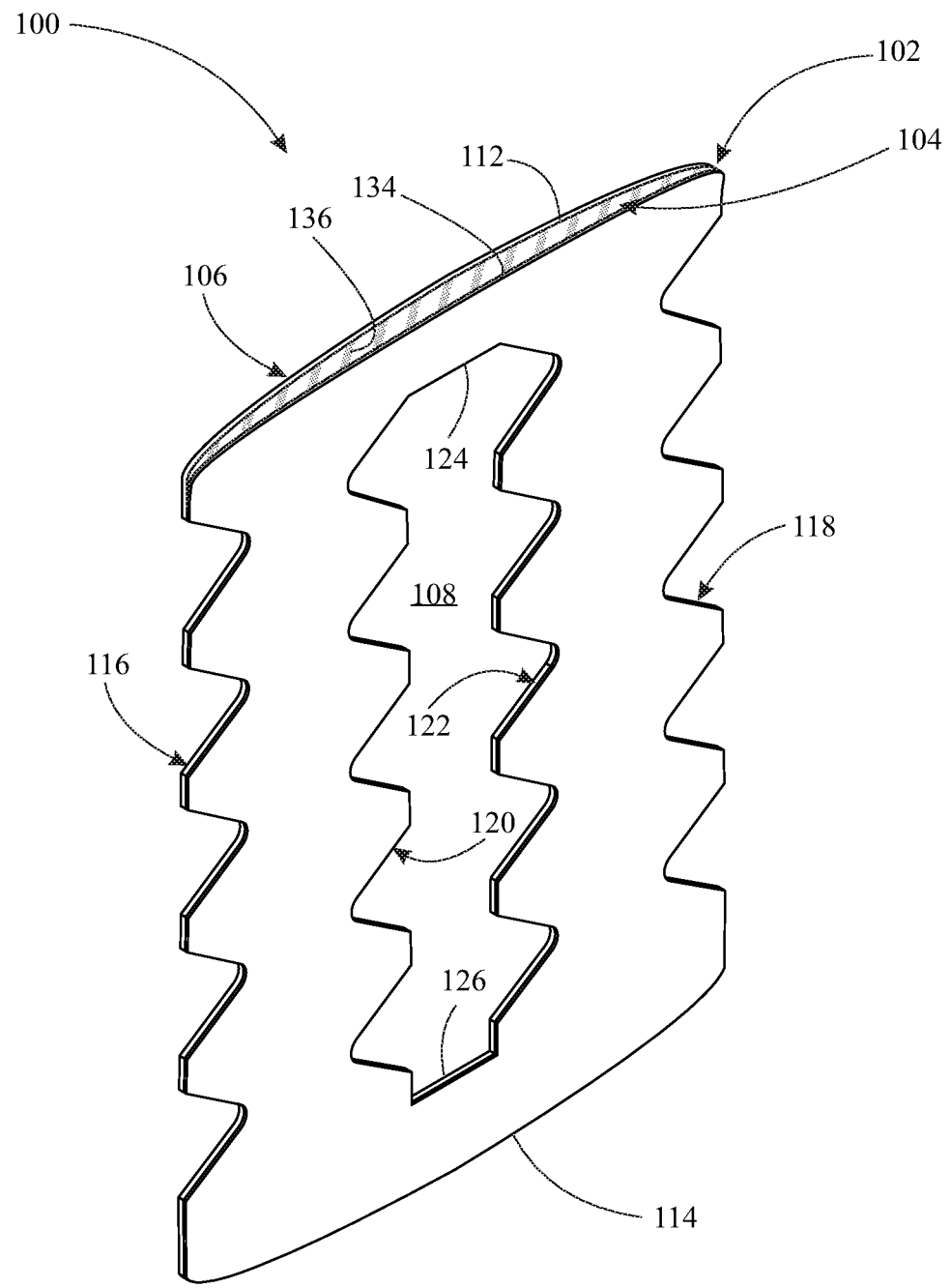
FIG. 2 presents a front isometric view of the spine support device originally introduced in FIG. 1.
Figure 3:
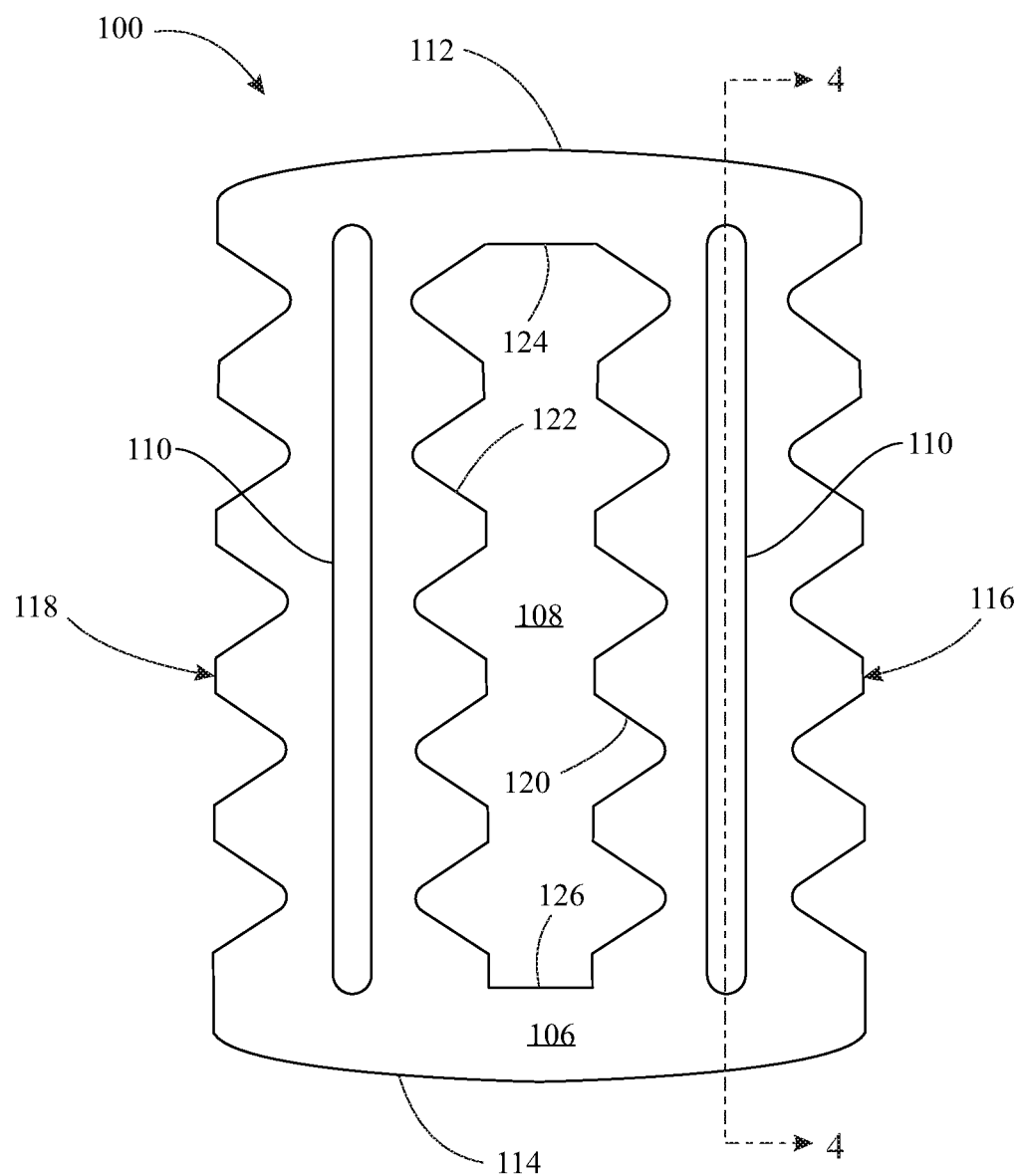
FIG. 3 presents a rear plan view of the spine support device originally introduced in FIG. 1.

Referring now particularly to FIGS. 5 and 6, the spine support device 100 may be applied to the person's back (B) so as to surround the cervical region (C1-C7) or the lumbar region (L1-L5) of the spinal vertebra (SV) of the individual donning the device. Further, the device 100 may be appropriately-sized for different sized individuals (e.g. smaller for youths than for adults). Still further, as shown in FIGS. 2 and 4, the support plate 102 may have a peel-off sheet 134 covering an adhesive layer 136 on the front face 104. The adhesive layer 136 is provided for releasably attaching the support plate 102 to the portion of the person's back B surrounding the spinal vertebra (SV) region visible through the central opening 108 in the support plate.

Referring now particularly to FIGS. 7-9 and 10-12, second and third exemplary implementations of the spine support device 100 are shown; generally designated 200 and 300. In accordance with aspects of the present invention, these two exemplary implementations generally include support plates, 202 and 302, respectively, each incorporating the same structure as the support plate 102 described and shown in accordance with the first exemplary implementation. Accordingly, structural details of each of the support plates 202, 302 shown in FIGS. 7-9 and 10-12 are identified by the same reference numerals as corresponding structural details of support plate 102, with the exception that the structural details are identified by reference numerals incorporating the respective prefixes "2" and "3." Accordingly, their structural details may be understood with reference to detailed description of the support plate 102. The respective second and third exemplary implementations differ from the first exemplary implementation, and from one another, vis-a-vis their stabilizing stirrup structures.

Figure 7:
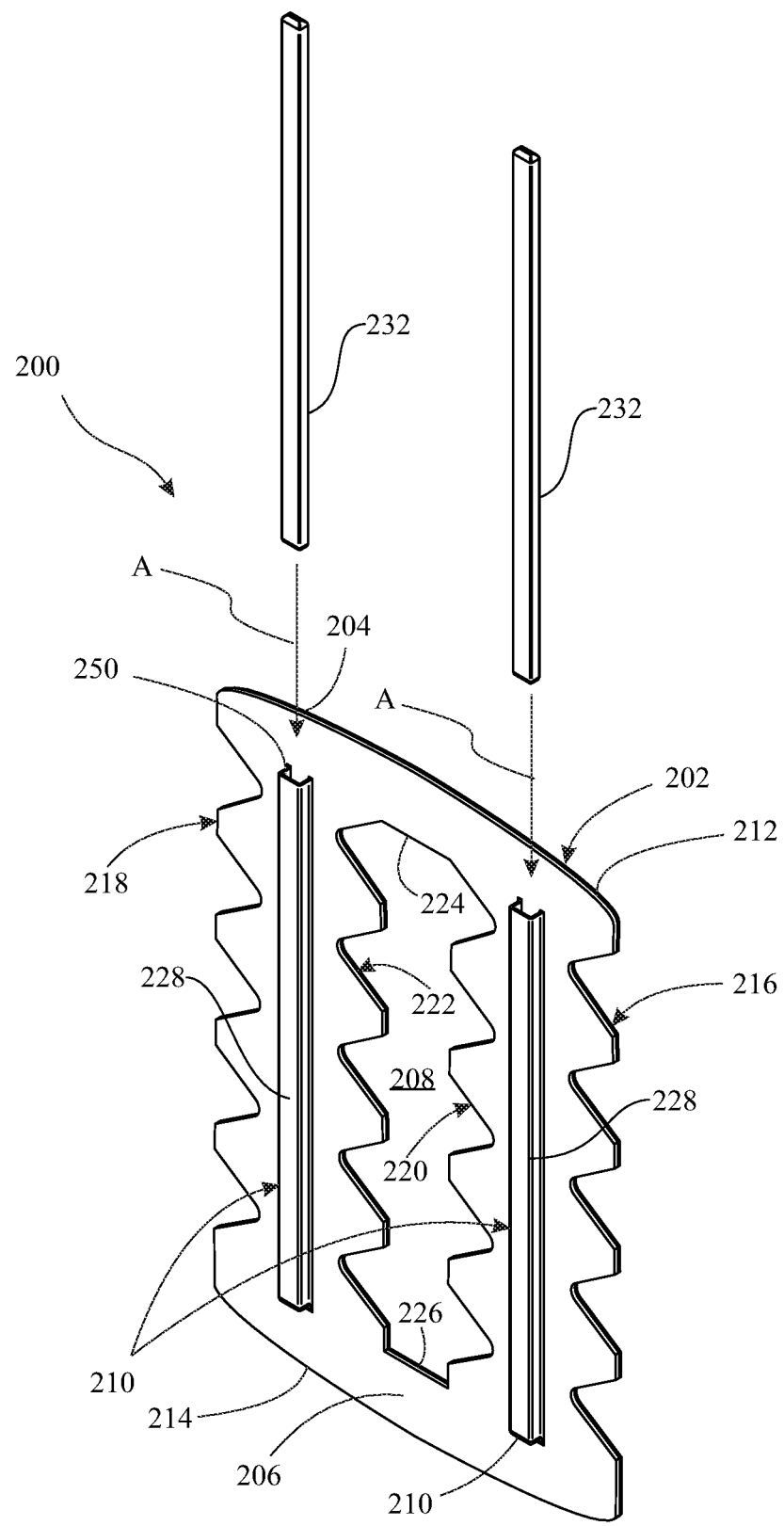
FIG. 7 presents a rear isometric view of a second exemplary implementation of a spine support device, in accordance with the present invention.
Figure 8:
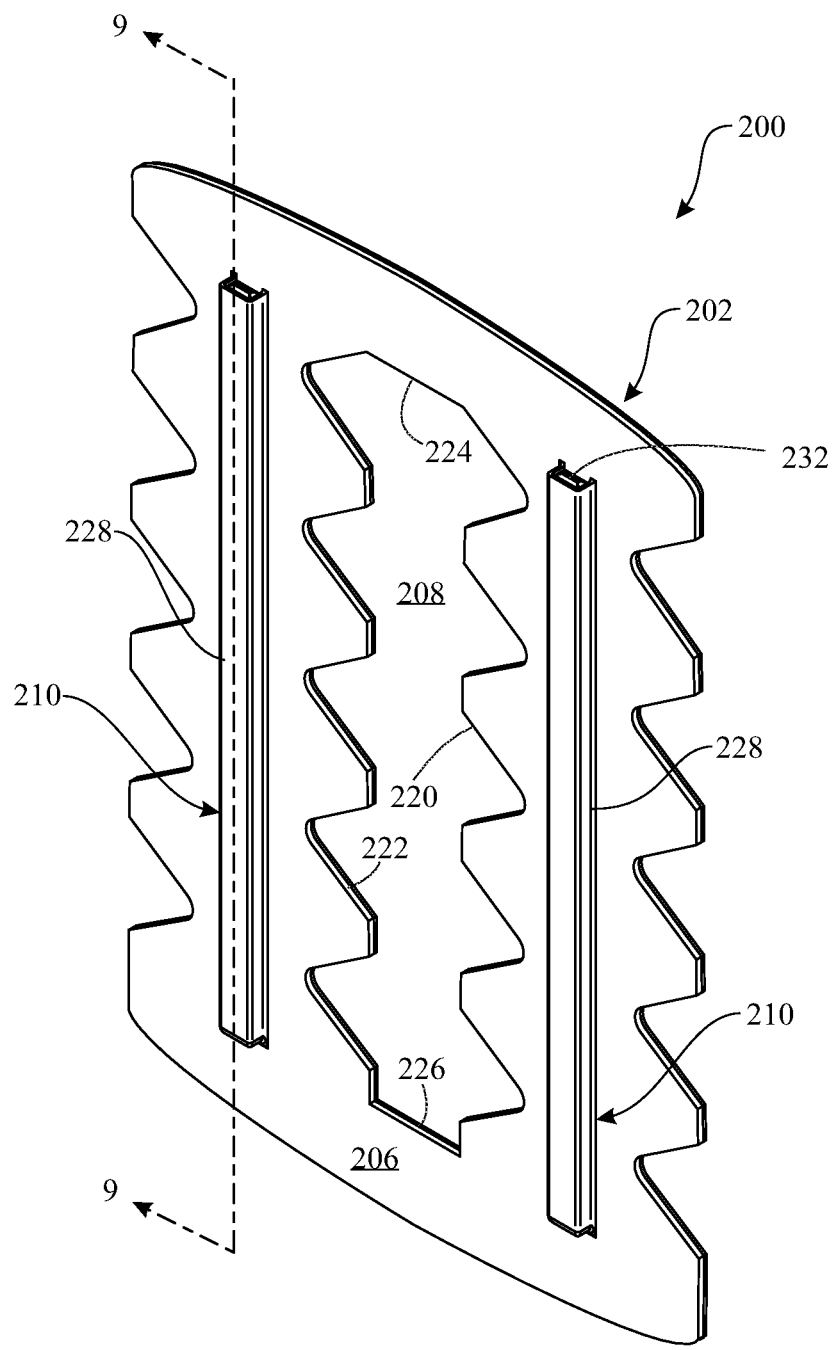
FIG. 8 presents an enlarged rear isometric view of the spine support device originally introduced in FIG. 7 having the pair of stabilizing stirrups with portions thereof shown in assembled form.
Figure 9:
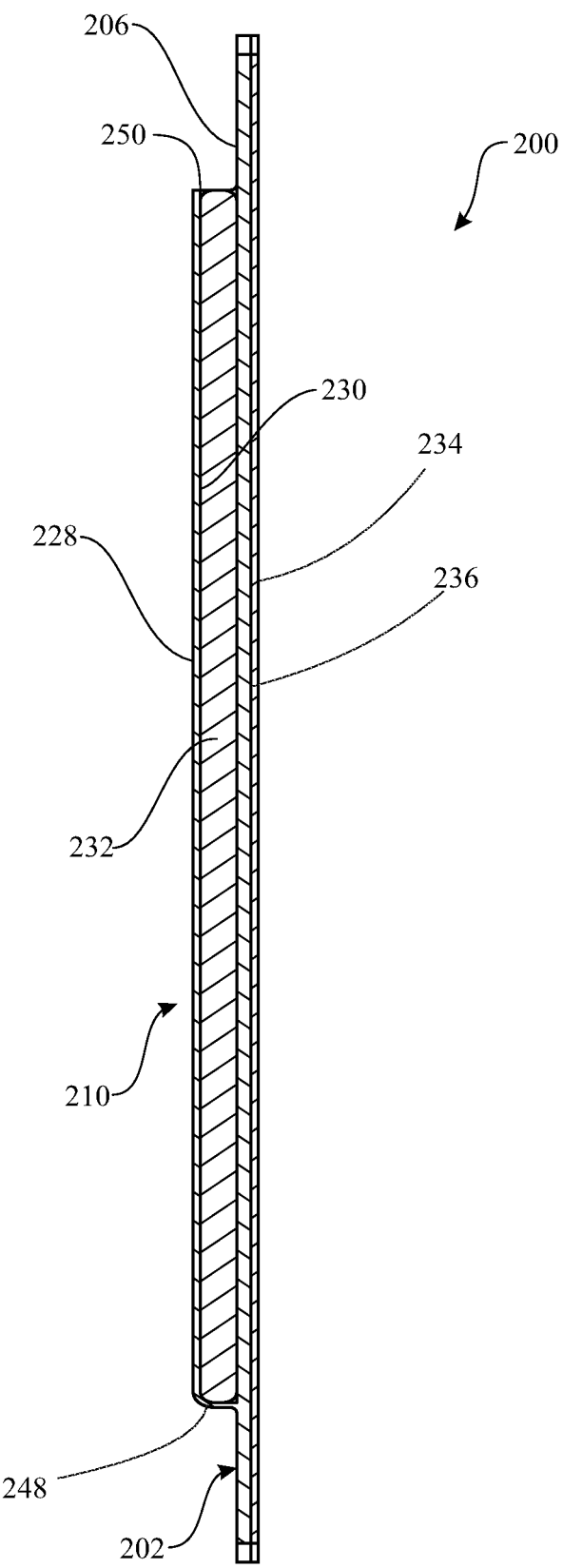
FIG. 9 presents an enlarged longitudinal sectional view of the spine support device of taken along section lines 9-9 of FIG. 8.

Referring now to FIGS. 7-9, there is shown the aforementioned second exemplary implementation of the spine support device 200 having a pair of stabilizing stirrups 210 protruding from the rear face 206 of the support plate 202 in a spaced-apart parallel relationship to one another and each in a spaced relationship from respective ones of the opposite peripheral side edge portions 216, 218 and the opposing inner side edge portions 220, 222 of the support plate so as to augment the support provided by the support plate when the latter is positioned in contact with the portion of the person's back. Each of the stabilizing stirrups 210 preferably includes an elongated outer body 228, or housing portion defining therethrough an elongated cavity 230, and an elongated inner body 232 disposed in the elongated cavity. In contrast to the spine support device 100 shown in the first exemplary implementation, the elongated outer body 228 of each stabilizing stirrup 210 may have a closed lower end 248 and an open upper end 250. The elongated inner body 232 may be inserted through the open upper end 250 into the elongated cavity 230 of the elongated outer body 228 and rest upon an interior surface of the closed lower end 248 thereof. The support plate 202 may have access openings (not shown) along the elongated cavity 244 so that the elongated inner body 232 can be used to administer prescription medication to the back of the person via the support plate. Furthermore, the support plate 202 itself and/or the adhesive layer 234 functioning as the attachment interface between the support plate and the lower back or neck of the individual user may be provided having medication integrated therewith for absorption into the underlying lower back or neck skin surface while the spine support device 500 is applied. As used herein, the term "medication" is meant to encompass one or more over-the-counter medications, prescription medications, vitamins, herbal and dietary supplements, and electrolytes. Furthermore, the medication may be configured for time-based delivery, heat and motion activation, etc.

As described hereinabove, a significant feature of the spine support devices 100, 200, 300 of the present invention is that they incorporate stabilizing stirrup constructions that enable a manufacturer or end user to easily vary the rigidity, or stiffness, imparted onto the corresponding support plates 102, 202, 302. It may be desirable to alter the stiffness based upon any of a number of factors. For example, the stiffness may be altered based upon the size of an individual or the severity of the individual's neck or back issues.

Figure 10:
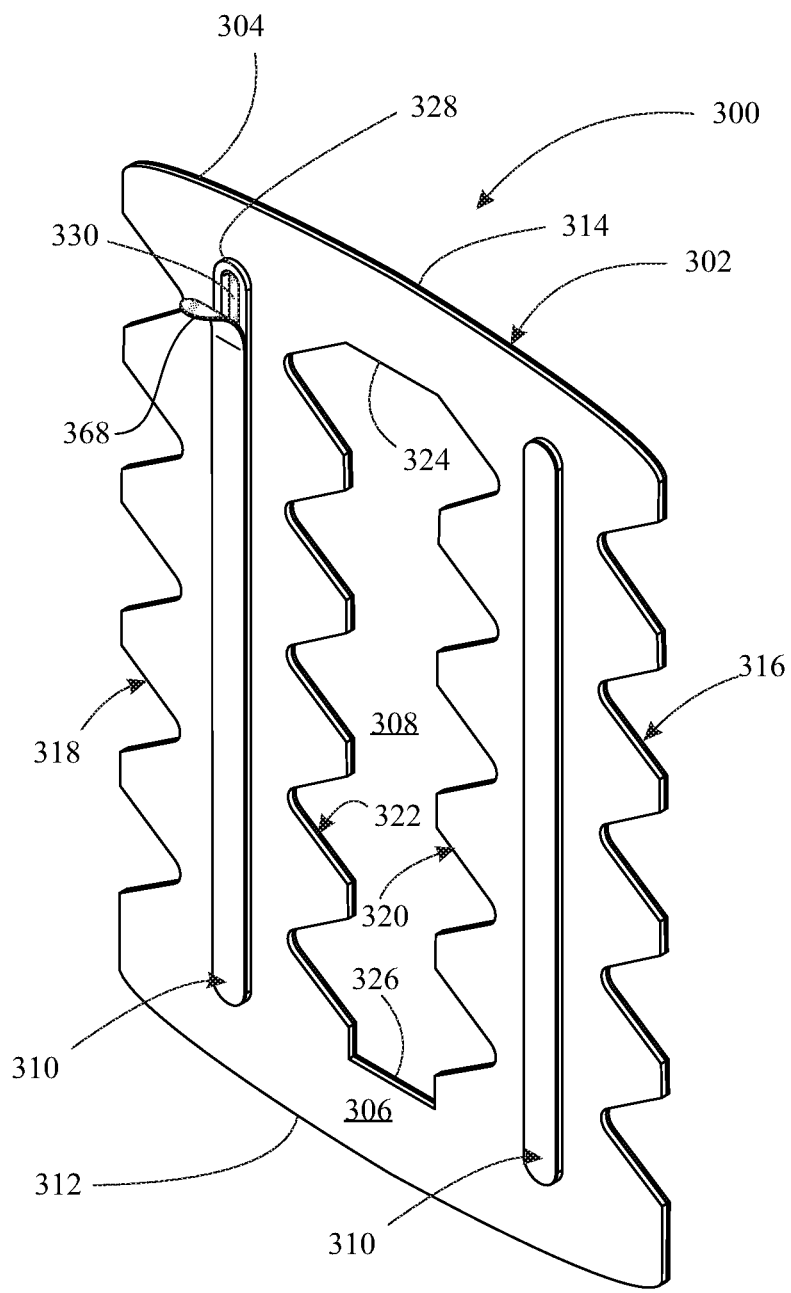
FIG. 10 presents a rear isometric view of a third exemplary implementation of a spine support device, in accordance with the present invention.
Figure 11:
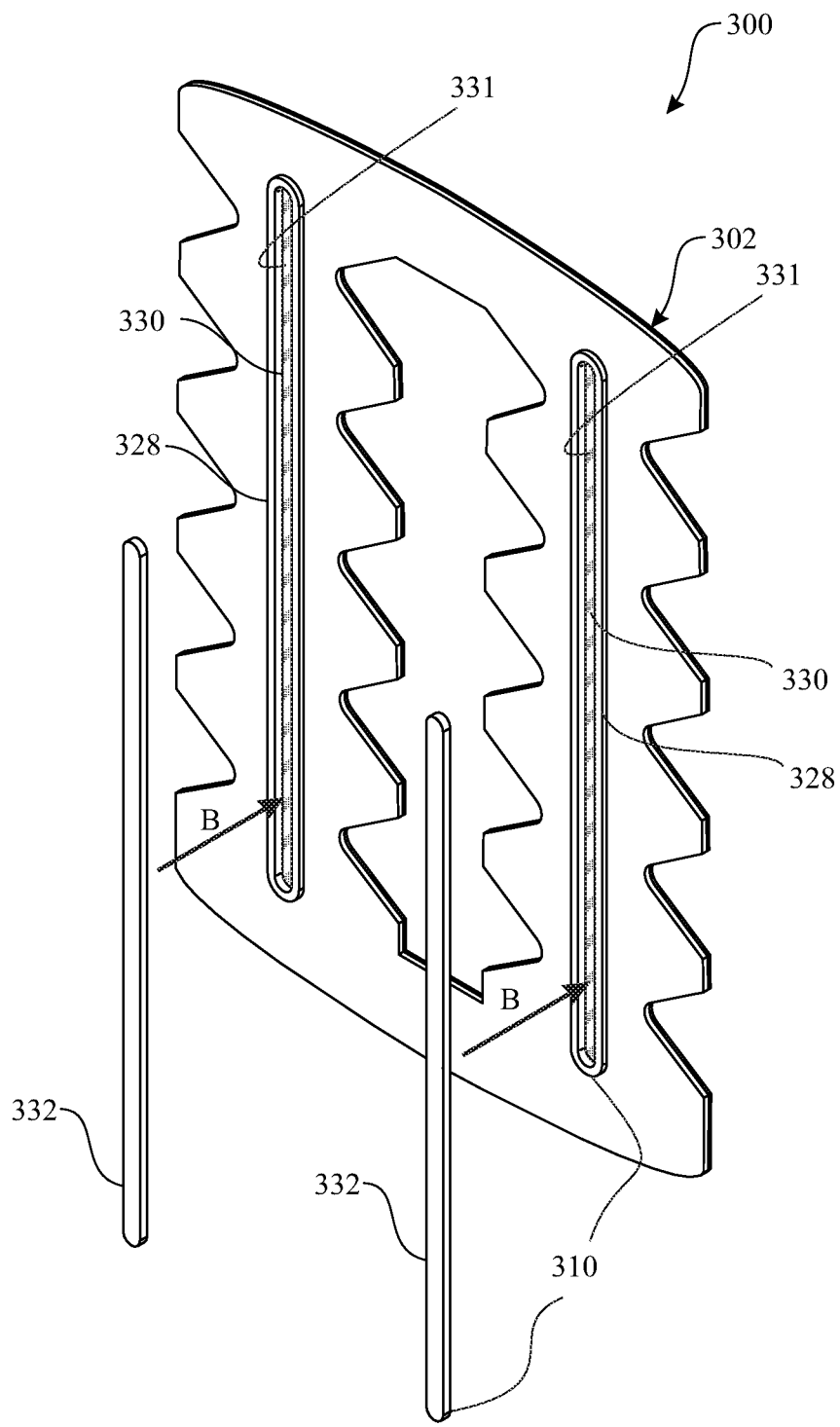
FIG. 11 presents a rear isometric view of the spine support device of FIG. 10 showing inner body portions 332, which may incorporate a medicinal component, aligned for insertion into respective stabilizing stirrup cavities.
Figure 12:
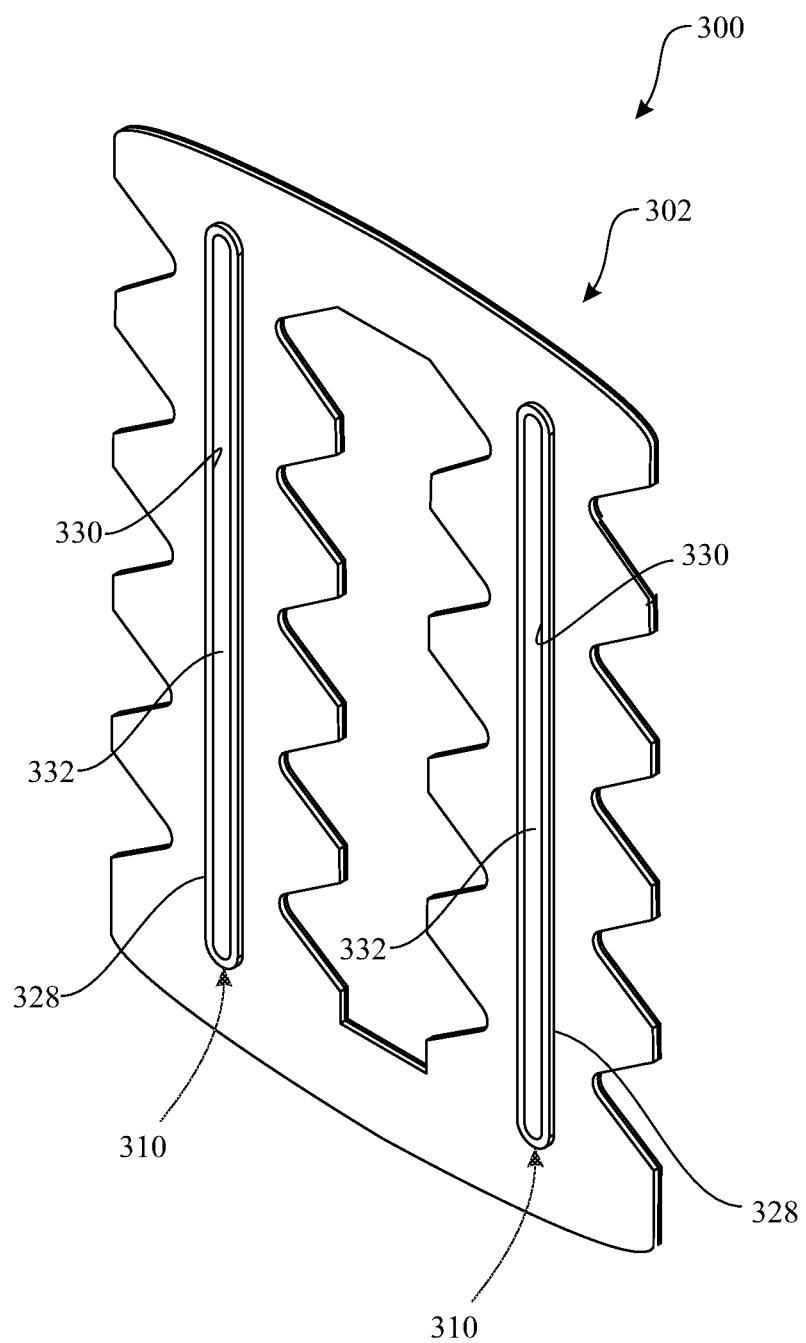
FIG. 12 presents a rear isometric view of the spine support device of FIG. 10 showing the inner body portions, which may be applicators incorporating a medicinal component, inserted into the stabilizing stirrup cavities.

Referring now to FIGS. 10-12, there is shown the third exemplary implementation of the spine support device 300 which has a pair of stabilizing stirrup subassemblies 310 protruding from the rear face 306 of the support plate 302 in a spaced-apart parallel relationship to one another and each in a spaced relationship from respective ones of the opposite peripheral side edge portions 316, 318 and the opposing inner side edge portions 320, 322 of the support plate so as to augment the support provided by the support plate when the latter is positioned in contact with the portion of the person's neck or back. Each of the stabilizing stirrup subassemblies 310 preferably includes an elongated outer body 328 in the form of a contiguous elliptically-shaped wall defining an elongated cavity 330, and an elongated inner body 332 disposed in the elongated cavity when the device 300 is fully assembled for use. As best shown in FIG. 10, prior to use the elongated cavity 330 is enclosed by a peel-off protective strip 368 disposed over the top of the outer body 328. Prior to use, the peel-off strips 368 may be removed and the elongated inner bodies 332 inserted into the respective cavities 330. Each elongated cavity 330 may incorporate an adhesive layer 331 (FIG. 11) for helping to retain the inner body 332 therein. However, the invention is not intended to be so limiting. In lieu of using an adhesive layer 331 to temporarily secure elongated inner body 332 within elongated outer body 330, applicant contemplates incorporating a mechanical attachment means such as a friction fit or snap fit configuration. Furthermore, in lieu of a chemical adhesive applicant contemplates using a hook-and-loop type system such as that sold under the tradename VELCRO. The elongated inner bodies 332, in addition to imparting rigidity for added support, may be provided in the form of a heated applicator, a cooled applicator or a medicated applicator.

Figure 13:
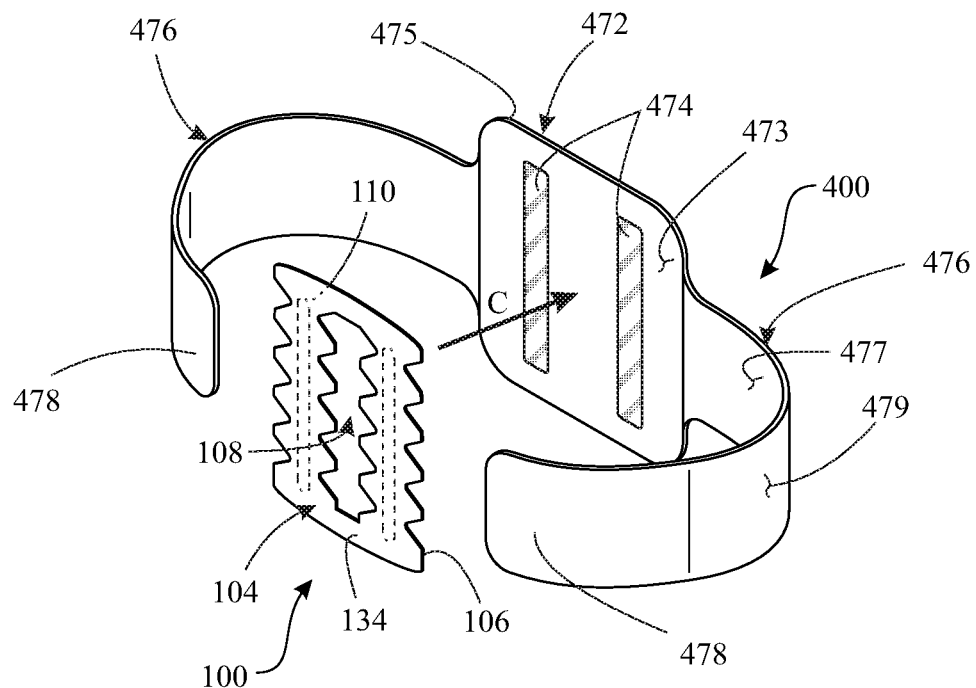
FIG. 13 presents a front isometric view of a spine support device system incorporating an applicator for enabling a single individual to apply the spine support device to the lower back without the aid of another individual, in accordance with a further aspect of the invention.
Figure 14:
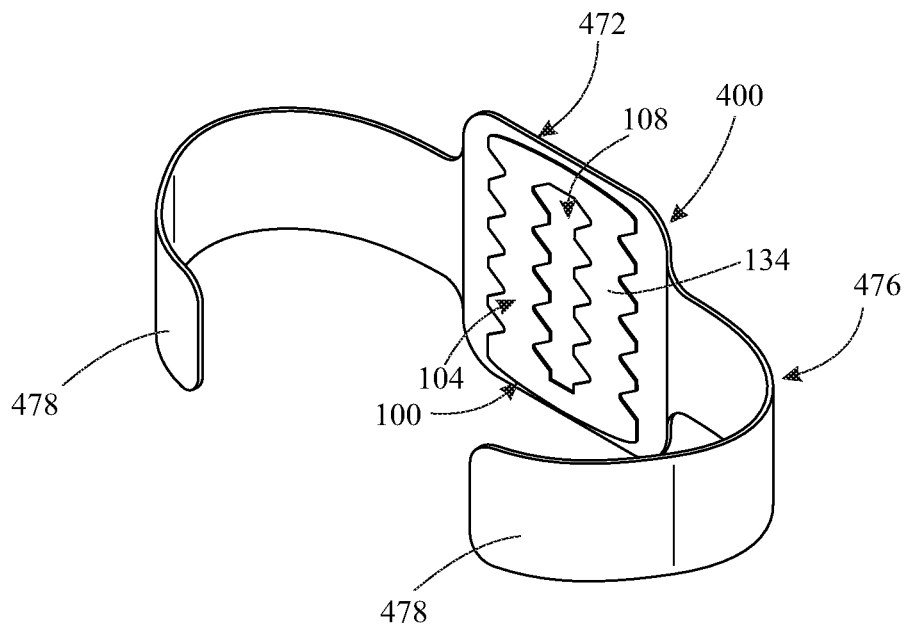
FIG. 14 presents a front isometric view of the spine support device system originally introduced in FIG. 13, showing the spine support device temporarily adhered to the applicator prior to application to the lower back of an individual.

Referring primarily to FIGS. 13 and 14, in accordance with a further aspect of the present invention, a spine support device applicator, generally designated by reference numeral 400, may be provided for aiding an individual user with the application of a spine support device, such as that designated by reference number 100, to their own back without requiring the aid of a second individual. While the spine support devices in accordance with the present invention may be easily affixed to the back or neck by a typical user without requiring an applicator or assistance from another individual, in some instances assistance may be required. For example, assistance may be required for elderly individuals and individuals that, for whatever reason, are unable to manipulate their bodies enough to properly affix the device to their neck or back. Accordingly, a spine support applicator is provided to enable such individuals to apply the device As best shown in FIG. 13, the spine support device applicator 400 includes a pair of flexible applicator arms 476 extending laterally outward from opposite side edges of applicator attachment panel 472, each having an inner-facing surface 477 and an outer-facing surface 479, and each terminating at a free hand-gripping end 478. The applicator attachment panel 472 is further defined by an inner-facing surface 473, an opposite outer-facing surface 475, and a pair of elongated vertically-oriented adhesive strips disposed upon the inner-facing surface. Although not shown, each of the elongated adhesive strips 474 is preferably provided having a removable peelable protective strip prior to use. Just prior to use, the removable peelable strips are removed and the spine support device 100 temporarily affixed to the inner-facing surface 473 (as shown in FIG. 14) by adhering the stabilizing stirrups 110 protruding outwardly from rear face 106 to the corresponding underlying adhesive layers 474 disposed upon the inner-facing surface of applicator attachment panel 472. Subsequently, in order to apply the spine support device 100 to, for example, the lower back, an individual would initially remove the peel off sheet 134 covering the adhesive layer 136 (see FIG. 2; peel off sheet 134 not shown in FIGS. 13-14) disposed upon the front face 104 of spine support device 100, grip the free ends 478 of the corresponding flexible applicator arms 476 and position the applicator attachment panel 476 rearwardly of the lower back, position the attachment panel such that the central opening 108 is aligned with the corresponding spinal length intended to be exposed through the opening (e.g. using a mirror for better precision), apply the spinal support device to the lower back by pulling the flexible applicator arms 476 forwardly, and finally pulling the flexible applicator arms rearwardly in order to detach the spine support device from the front face 473 of the applicator attachment panel 472—leaving the support device adhered to the lower back. Preferably, this is accomplished by choosing adhesives disposed upon the applicator panel 472 and front face 104 of spine support device 100 such that the normal (i.e. perpendicular) force required to detach the applicator panel from the stabilizing stirrups 110 of the spine support device 100 is less than the respective force required to detach the front face of the spine support device 100 from the individual's back.

Figure 15:
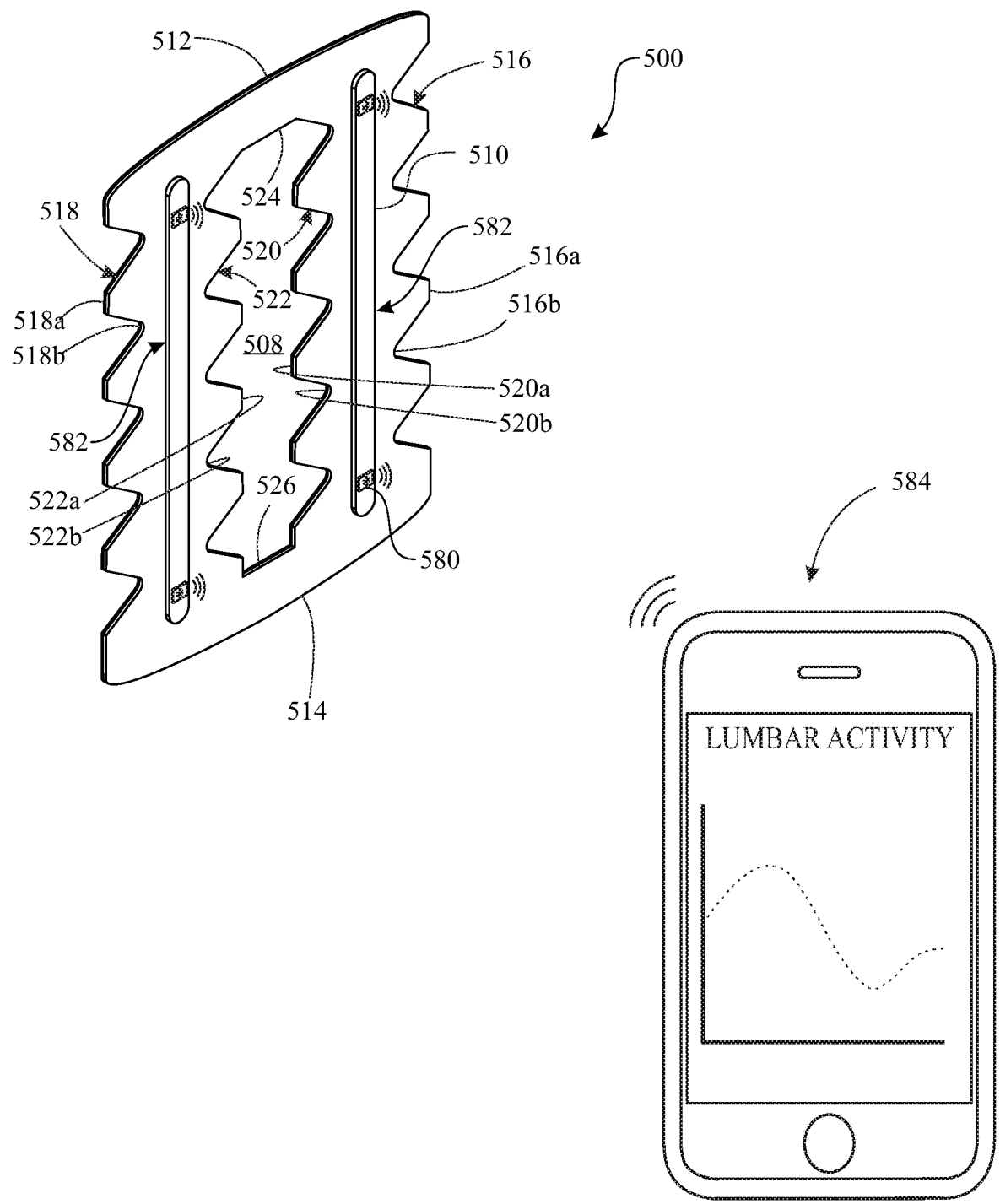
FIG. 15 presents a rear isometric view of a further exemplary implementation of a spine support device 500 incorporating vibration-imparting mechanisms 580 into the support stirrups 510, for wireless communication with a portable communication device 584, in accordance with the present invention.

Referring now to FIG. 15, in accordance with a further exemplary implementation a spine support device, generally designated 500, may incorporate one or more vibration sources 580 for selectively imparting a vibration to the back or neck area via the spine support device 500 once it has been adhesively affixed to the user's body. Miniature vibration motors are well known in the electronic arts. There are two basic types of vibration motor. An eccentric rotating mass vibration motor (ERM) uses a small unbalanced mass on a DC motor, which creates a force that translates to vibrations when it rotates. A linear resonator actuator (LRA) contains a small internal mass attached to a spring, which creates force when driven. A variety of different vibration motor form factors are commercially available. Preferably, the present invention incorporates a so-called "coin" or "pancake" type form factor. By way of example, the present invention may incorporate self-adhesive vibration micro motors (Rated Voltage: DC 3V; Rated Speed: 12000 RPM) having a flat coin button-type form factor. However, the invention is not intended to be so limiting. Depending upon the desired force any of a variety of miniature/small vibration motor form factors and structures is contemplated for use.

The vibrational energy generated by the vibratory sources 580 is transmitted, via the device 500, to the back or neck of the user. Imparting a vibrational energy may provide improved blood flow/circulation proximate to the vibratory sources 582, improved pain control, and improved irritating sensation control (e.g. control of burning or itching sensations during the provision of medications that create a burning or itching sensation when administered to the user), and the like. By way of example, pairs of vibratory sources may be integrated at opposite end portions of each of the stabilizing stirrups 510. A Bluetooth Surface Mount Device (SMD) module (not shown), such as those commercially available from Roving Networks of Los Gatos, Calif., may be used to interface the motor and enable it to receive notifications from a mobile phone or other portable wireless smart device 584. In this manner, the electronic communication device 584 may communicate wirelessly with the vibratory sources 582 to selectively actuate the vibratory sources between ON and OFF states. As will be apparent to those skilled in the art, a smart device application may reside on the electronic communication device 584 to enable a user to perform the selective actuation of the vibratory sources.

Still referring to FIG. 15, sensors (not shown) having sense capabilities and the ability to deform with one or more rotational degrees of freedom may be integrated into the stabilizing stirrups 510 of spine support device 500 in order to measure various bending and twisting forces upon the stabilizing stirrups while the spine support device is being donned. The sensors may include angular displacement sensors, strain sensors, compressive force sensors, haptic actuator sensors, as well as others, in various configurations. Furthermore, the sensors may be embedded within the stirrups 510 or disposed upon an exterior surface of the stirrups. Additional electronic circuitry and electronic devices well known in the electronic arts may be incorporated in order to facilitate wireless communication with an application run on a smart phone 584 or other portable electronic device. In this manner, the spine support device 500 may be equipped to provide spinal activity feedback for review by an individual donning the spine support device. Furthermore, by using Bluetooth (or any other available wireless communication means) to communicate data, in conjunction with a corresponding software application residing on the portable electronic device 584, the stabilizing stirrups 582 may be employed to sense different movements of the spine and the information analyzed and recorded/stored within a database. Also, it is contemplated that the sensors may be integrated directly into the support plate in lieu of, or in addition to, sensor integration into the stabilizing stirrups 582.

To recapitulate, the several exemplary embodiments of the spine support device, as described above, incorporate design features that accommodate the natural anatomy of the spine. The support plate of the spine support device incorporates shapes that allow for natural bending and rotational movement that is generated by the spine to occur, facilitating more degrees of freedom which, in turn, allow the spine to move in a manner that is anatomically correct. Stabilizing stirrups are provided on the support plate having a sufficient degree of stiffness, or firmness, to provide the spine with the stability needed for proper alignment and support. The support plate and stabilizing stirrups may be manufactured using conventional fabrication techniques and from suitable materials, such as conventional plastics.

Furthermore, there are multiple potential applications for the spine support device. It can be used in the medical/healthcare field to treat and reduce back pain. It can be utilized in the workplace to promote good health and reduce work stoppages. It can also be utilized in all types of athletic/recreational activities ranging from the novice person who just wants to walk to the various activities and endeavors of professional and Olympic athletes. The field of golf is one perfect fit for the device. However, its applications encompass all areas of sports including, but not limited to, tennis, biking and running.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A spinal support device, comprising:
   a pliable support plate partially defined by a contiguous peripheral edge adjoining opposite front and rear pliable support plate faces, and by a longitudinal opening extending completely through the pliable support plate and overlying a corresponding predetermined spine segment of a spinal support device user's spine when the spinal support device is adhered to a posterior surface of the spinal support device user's body during use, wherein the predetermined spine segment of the spinal support device user's spine includes a contiguous series of individual spinal vertebra and interconnecting facets of said contiguous series of individual spinal vertebra;
   an adhesive layer disposed upon the pliable support plate front face for facilitating releasable adhesive attachment of the pliable support plate directly to said posterior surface of the spinal support device user's body; and
   a pair of vertically-oriented longitudinal stabilizing stirrups integrated with the rear face of the pliable support plate in a spaced-apart parallel relationship to one another, each one of said pair of vertically-oriented longitudinal stabilizing stirrups having a rigidity adequate to impart a predefined desired degree of spinal support to said predetermined spine segment in a manner limiting spinal flexion thereof, thereby augmenting support provided by the pliable support plate following said releasable adhesive attachment of the front face of the pliable support plate to the posterior surface of the spinal support device user's body, the pair of vertically-oriented longitudinal stabilizing stirrups enabling freedom of rotational movement of the corresponding predetermined spine segment of the spinal support device user's spine extending beneath an area of the posterior surface of the spinal support device user's body that remains exposed through the vertically-oriented longitudinal opening of the pliable support plate after the spinal support device is adhered to the posterior surface of the spinal support device user's body.

2. The spinal support device as recited in claim 1, further comprising a removable protective sheet adhered to the adhesive layer disposed upon the front face of the pliable support plate, such that the adhesive layer is interposed between the front face of the pliable support plate and an interior surface of the removable protective sheet prior to adhering the pliable support plate of the spinal support device to the posterior surface of the spinal support device user's body.

3. The spinal support device as recited in claim 2 wherein the adhesive layer disposed upon the front face of said pliable support plate further comprises at least one of a medicated chemical composition and a non-medicated chemical composition.

4. The spinal support device as recited in claim 1 wherein said pliable support plate contiguous peripheral edge adjoining the front and rear pliable support plate faces further comprises peripheral side edge portions defining mirror image notched edge profiles.

5. The spinal support device as recited in claim 4, wherein said contiguous pliable support plate interior edge further comprises interior side edge portions defining mirror image notched edge profiles.

6. The spinal support device as recited in claim 5, wherein the notched edge profiles of the peripheral side edge portions of said pliable support plate contiguous peripheral edge and the corresponding notched edge profiles of said contiguous pliable support plate interior side edge portions are laterally aligned with one another.

7. The spinal support device as recited in claim 6, wherein the contiguous peripheral edge of said pliable support plate further comprises a pair of opposite upper and lower peripheral edge portions each having a convex edge profile.

8. The spinal support device as recited in claim 1 wherein the adhesive layer disposed upon the front face of said pliable support plate further comprises at least one of a medicated chemical composition and a non-medicated chemical composition.

9. The spinal support device as recited in claim 1, further comprising a spinal support device applicator at least partially defined by a spinal support device applicator attachment panel having a pair of flexible applicator arms extending laterally outward from opposite sides thereof, the spinal support device applicator attachment panel having a pair of vertically-oriented adhesive strips disposed thereon and positioned for releasable attachment of said spinal support device stabilizing stirrups thereto, wherein, during the process of affixing the spinal support device to the posterior surface of the spinal support device user's body, the user adheres the pair of spaced-apart, vertically-oriented longitudinal stabilizing stirrups integrated with the rear face of the pliable support plate to the corresponding pair of vertically-oriented adhesive strips disposed on the spinal support device applicator, grips free ends of said flexible applicator arms, and positionally manipulates the spinal support device applicator to adhere the spinal support device to the posterior surface of the user's body.

10. The spinal support device as recited in claim 9, further comprising a pair of peel-off protective coverings disposed over said pair of vertically-oriented adhesive strips disposed upon said spinal support device applicator attachment panel.

11. The spinal support device as recited in claim 1, further comprising at least one vibration-imparting mechanism integrated with at least one of said pair of vertically-oriented longitudinal stabilizing stirrups integrated with the rear face of said pliable support plate.

12. The spinal support device as recited in claim 11, wherein said vibration-imparting mechanism further comprises:
   a motor; and
   a Bluetooth surface mount device (SMD) module for enabling wireless communication between said vibration-imparting mechanism and a remote wireless communication device,
   wherein, said Bluetooth SMD module enables actuation of said vibration-imparting mechanism via said remote wireless communication device.

13. The spinal support device as recited in claim 1, further comprising at least one sensor integrated into at least one of said pair of vertically-oriented longitudinal stabilizing stirrups integrated with the rear face of said pliable support plate, said at least one sensor having sensing capabilities and the ability to deform with one or more rotational degrees of freedom to thereby enable measurement of at least one of bending forces and twisting forces imparted upon said at least one vertically-oriented longitudinal stabilizing stirrup.

14. The spinal support device as recited in claim 13, wherein said at least one sensor integrated into at least one of said pair of vertically-oriented longitudinal stabilizing stirrups further comprises at least one of:
   an angular displacement sensor;
   a strain sensor;
   a compressive force sensor; and
   a haptic sensor.

15. The spinal support device as recited in claim 14, further comprising:
   a wireless smart device; and
   an application running on said wireless smart device for facilitating communication between said wireless smart device and said at least one sensor,
   wherein, said application functions to collect and analyze lumbar activity data from said at least one sensor integrated into said at least one vertically-oriented longitudinal stabilizing stirrup while said spinal support device is adhered to the posterior surface of the user's body.

16. A spinal support device, comprising:
   a support plate having adequate pliability to conform with a posterior surface of a body of an individual, the support plate bounded exteriorly by a continuous peripheral edge having opposite longitudinally-oriented peripheral edge portions, the support plate bounded interiorly by a continuous interior edge having opposing longitudinally-oriented interior edge portions, the continuous interior edge defining a central longitudinal opening through the support plate, the opposite longitudinally-oriented peripheral edge portions and the corresponding opposing longitudinally-oriented interior edge portions each having an edge profile defining a series of spaced-apart notches, the series of spaced-apart notches along the opposite longitudinally-oriented peripheral edge portions and the series of spaced-apart notches along the opposing longitudinally-oriented interior edge portions all laterally aligned with one another, the central longitudinal opening through the support plate sized and shaped to visibly expose a desired area of said posterior surface of the body of the individual overlying a segment of the individual's spine when a front surface of the support plate is adhesively attached to said posterior surface of the body of the individual, the spine segment of the individual including a contiguous series of individual spinal vertebra and spinal vertebra-interconnecting facets, the laterally-aligned spaced-apart notches along the longitudinally-oriented peripheral edge portions of the support plate, and the corresponding opposing longitudinally-oriented interior edge portions of the support plate, together, enabling spinal twisting movement about a spinal axis along said spine segment;
   an adhesive layer disposed upon a support plate front face for facilitating releasable adhesive attachment of the support plate directly to the posterior surface of the body of the individual;
   a removable protective sheet disposed over said adhesive layer; and
   a pair of longitudinally-oriented elongated rigid support rod structures disposed in a spaced-apart parallel relationship with one another upon a rear face of said support plate and located on opposite sides of the central longitudinal opening of the support plate, the pair of longitudinally-oriented elongated rigid support rod structures having adequate rigidity to restrict flexion and extension of said spine segment.

17. The spinal support device as recited in claim 16 wherein said adhesive layer disposed upon the front face of the support plate further comprises at least one of a medicated chemical composition and a non-medicated chemical composition.

18. The spinal support device as recited in claim 16, further comprising a vibration-generating mechanism integrated into at least one of said longitudinally-oriented elongated rigid support rod structures.

19. The spinal support device as recited in claim 16, further comprising at least one sensor integrated into at least one of said longitudinally-oriented elongated rigid support rod structures, said at least one sensor having sense capabilities and deformable during corresponding flexion and extension deformation of said at least one longitudinally-oriented elongated rigid support rod structure.

20. The spinal support device as recited in claim 19, further comprising:
   a wireless smart device; and
   an application running on said wireless smart device for enabling and facilitating communication between said wireless smart device and said at least one sensor integrated into at least one of said longitudinally-oriented elongated rigid support rod structures,
   wherein, the application running on said wireless smart device functions to collect and analyze lumbar activity data from said at least one sensor integrated into at least one of said longitudinally-oriented elongated rigid support rod structures, while said spinal support device is adhered to the posterior surface of the body of the individual.

* * * * *